United States Patent

Weber et al.

(10) Patent No.: US 6,362,142 B1
(45) Date of Patent: Mar. 26, 2002

(54) DETERGENT MIXTURES CONTAINING ESTER QUATS, CHITOSAN AND/OR CHITOSAN DERIVATIVES AND PROTEIN HYDROLYZATES

(75) Inventors: Peter Weber, Monheim; Bernd Fabry, Korschenbroich, both of (DE)

(73) Assignee: Cognis Deutschland GmbH, Dusseldorf (DE)

( * ) Notice: Subject to any disclaimer, the term of this patent is extended or adjusted under 35 U.S.C. 154(b) by 0 days.

(21) Appl. No.: 09/463,133

(22) PCT Filed: Jul. 8, 1998

(86) PCT No.: PCT/EP98/04244

§ 371 Date: Apr. 17, 2000

§ 102(e) Date: Apr. 17, 2000

(87) PCT Pub. No.: WO99/03959

PCT Pub. Date: Jan. 28, 1999

(30) Foreign Application Priority Data

Jul. 17, 1997 (DE) ......................... 197 30 649

(51) Int. Cl.$^7$ ................. C11D 1/62; C11D 3/382; C11D 3/22

(52) U.S. Cl. ............. 510/119; 510/123; 510/130; 510/135; 510/405; 510/433; 510/463; 510/470; 510/504

(58) Field of Search ............... 510/119, 130, 510/135, 405, 433, 470, 504, 123, 490, 463

(56) References Cited

U.S. PATENT DOCUMENTS

| | | | |
|---|---|---|---|
| 4,172,887 A | 10/1979 | Vanlerberghe et al. | 424/70 |
| 4,765,976 A | 8/1988 | Grollier et al. | 424/70 |
| 5,374,716 A | 12/1994 | Biermann et al. | 536/18.6 |
| 5,494,659 A | 2/1996 | Salka et al. | 424/70.13 |
| 5,576,425 A | 11/1996 | Hill et al. | 536/18.6 |
| 5,656,200 A | 8/1997 | Boettcher et al. | 252/307 |
| 5,718,891 A | 2/1998 | Prat et al. | 424/70.28 |
| 5,797,987 A | 8/1998 | Rossio | 106/14.12 |
| 5,945,299 A | 8/1999 | Von Kries et al. | 435/68.1 |
| 5,962,663 A | 10/1999 | Wachter et al. | 536/20 |
| 5,981,450 A | * 11/1999 | Fabry et al. | 510/127 |

FOREIGN PATENT DOCUMENTS

| | | |
|---|---|---|
| CA | 2 101 079 | 8/1994 |
| DE | 1 165 574 | 3/1964 |
| DE | 20 24 051 | 5/1986 |
| DE | 37 13 099 | 10/1987 |
| DE | 43 08 794 | 4/1994 |
| DE | 195 02 168 | 6/1996 |
| DE | 195 02 167 | 8/1996 |
| DE | 195 37 001 | 3/1997 |
| DE | 44 42 987 | 4/1997 |
| DE | 196 04 180 | 8/1997 |
| EP | 0 301 298 | 2/1989 |
| FR | 22 52 840 | 12/1978 |
| FR | 27 01 266 | 8/1994 |
| GB | 962 919 | 7/1964 |
| GB | 1 333 475 | 10/1973 |
| WO | WO90/03977 | 4/1990 |
| WO | WO91/01295 | 2/1991 |
| WO | WO94/16677 | 8/1994 |
| WO | WO95/05802 | 3/1995 |
| WO | WO97/06780 | 2/1997 |
| WO | WO97/18033 | 5/1997 |

OTHER PUBLICATIONS

R. Puchta, Tens. Surf. Det., 30 (1993) pp. 186–191.
M. Brock, Tens. Surf. Det., 30 (1993) pp. 394,396,398.
R. Lagerman, et al, J. Am. Oil. Chem. Soc., 71 (1994) pp. 97–99.
I. Shapiro, et al, Cosm. Toil., 109 (1994) pp. 77–78,80.
Ullmann's Ency. of Ind. Chem., 5th Ed., Weinheim, Verlag Chemie, vol.46, (1986) pp. 231–332.
B. Gesslein, Happi, 27 (1990) p. 57.
O. Skaugrud, Drug Cosm. Ind., 148 (1991) pp. 24,26,30.
E. Onsoyen, et al, Seifen–Öle–Fette–Wachse, 117 (1991) pp. 633–637.
Sannan, et al, Makromol Chem., 177 (1976) pp. 3589–3600.
Schuster, et al, Seifen–Öle–Fette–Wachse, 108 (1982) pp.177–184.
Schuster, et al, Cosm. Toil., 99 (1984) pp. 63–74.
Steisslinger, Parf. Kosm., 72 (1991) pp.556–557 pp.560–561 pp. 565–566.
Aurich, et al, Tens. Surf. Det., 29 (1992) pp. 389–395.
Ploog, Seifen–Öle–Fette–Wachse, 198 (1982) pp. 373–376.
O'Lenick, Jr., et al, Happi, Nov. (1986) pp. 70,72,74.
Holzman, et al, Tens. Surf. Det., 23 (1986) pp. 309–313.
Bibo, et al, Soap Cosm. Chem. Spec., Apr.(1990) pp.46–50 p.116.
Ellis, et al., Euro. Cosm., 1 (1994) pp. 14–16.
"Kosmetische Faerbemittel", Farbstoffkommission der Deutschen Forschungsgemeinschaft, Verlag Chemie, Weinheim, (1984) pp. 81–106.

\* cited by examiner

*Primary Examiner*—Charles Boyer
(74) *Attorney, Agent, or Firm*—John E. Drach; Steven J. Trzaska

(57) ABSTRACT

A surface-active composition useful for cleaning various types of substrates such as articles of clothing, various types of hard surfaces, as well as, human hair and skin, the composition containing: (a) an esterquat; (b) a chitosan and/or chitosan derivative; and (c) a protein hydrolyzate.

19 Claims, No Drawings

DETERGENT MIXTURES CONTAINING ESTER QUATS, CHITOSAN AND/OR CHITOSAN DERIVATIVES AND PROTEIN HYDROLYZATES

BACKGROUND OF THE INVENTION

This invention relates to detergent mixtures containing esterquats, chitosans and protein hydrolyzates and optionally alkyl glycosides and/or betaines and to the use of the mixtures for the production of surface-active compositions.

Large numbers of surfactant mixtures used for various applications are known from the prior art. In the field of raw materials for detergents and cosmetics, however, there is a need for concentrated surfactant premixes distinguished by good cleaning and conditioning properties on the one hand with respect to synthetic fibers, i.e. textiles and their precursors, and on the other hand with respect to natural (keratin) fibers, i.e. human hair. Another requirement is that the products should have optimal dermatological compatibility so that even particularly sensitive consumers are in no real danger of suffering skin irritation either directly through handling the products or indirectly through contact with the treated fibers.

Accordingly, the complex problem addressed by the invention was to provide new detergent mixtures both for the detergent industry and for the cosmetics industry which would be distinguished by particularly high dermatological compatibility, favorable skin and textile cleaning and rewetting behavior and an excellent conditioning effect on synthetic and natural fibers.

DESCRIPTION OF THE INVENTION

The present invention relates to detergent mixtures containing (a) esterquats,
(b) chitosan and/or chitosan derivatives and
(c) protein hydrolyzates.

It has surprisingly been found that the detergent mixtures according to the invention not only show particularly high dermatological compatibility, they also develop a particularly high cleaning performance both with respect to textiles and with respect to skin and hair. In addition, not only do they provide textiles and hair with a pleasant soft feel, they also reduce the static charge between the fibers.

Esterquats

"Esterquats" (component a) are generally understood to be quaternized fatty acid triethanolamine ester salts. These are known substances which may be obtained by the relevant methods of preparative organic chemistry., cf. International patent application WO 91/01295 (Henkel). According to this document, triethanolamine is partly esterified with fatty acids in the presence of hypophosphorous acid, air is passed through and the reaction product is quatemized with dimethyl sulfate or ethylene oxide. Overviews on this subject have been published, for example, by R. Puchta et al. in Tens. Surf. Det., 30, 186 (1993), by M. Brock in Tens. Surf, Det. 30, 394 (1993), by R. Lagerman et al. in J. Am. Oil. Chem. Soc., 71, 97 (1994) and by I. Shapiro in Cosm. Toll., 109, 77 (1994).

The quaternized fatty acid triethanolamine ester salts correspond to formula (I):

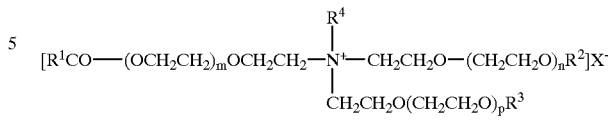

in which $R^1CO$ is an acyl group containing 6 to 22 carbon atoms, $R^2$ and $R^3$ independently of one another represent hydrogen or have the same meaning as $R^1CO$, $R^4$ is an alkyl group containing 1 to 4 carbon atoms or a $(CH_2CH_2O)qH$ group, m, n and p together stand for 0 or numbers of 1 to 12, q is a number of 1 to 12 and X is halide, alkyl sulfate or alkyl phosphate. Typical examples of esterquats which may be used in accordance with the invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained for example in the pressure hydrolysis of natural fats and oils. Technical $C_{12/18}$ cocofatty acids and, in particular, partly hydrogenated $C_{16/18}$ tallow or palm oil fatty acids and high-elaidic $C_{16/18}$ fatty acid cuts are preferably used. To produce the quaternized esters, the fatty acids and the triethanolamine may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9 and are derived from technical $C_{16/18}$ tallow or palm oil fatty acid (iodine value 0 to 40). In performance terms, quaternized fatty acid triethanol amine ester salts corresponding to formula (I), in which $R^1CO$ is an acyl group containing 16 to 18 carbon atoms, $R^2$ has the same meaning as $R^1CO$, $R^3$ is hydrogen, $R^4$ is a methyl group, m, n and p stand for 0 and X stands for methyl sulfate, have proved to be particularly advantageous.

Other suitable esterquats besides the quatemized fatty acid. triethanolamine ester salts are quaternized ester salts of fatty acids with. diethanolalkyamines corresponding to formula (II):

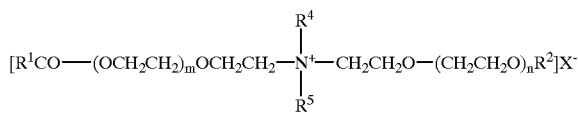

in which $R^1CO$ is an acyl group containing 6 to 22 carbon atoms, $R^2$ is hydrogen or has the same meaning as $R^1CO$, $R^4$ and $R^5$ independently of one another are alkyl groups containing 1 to 4 carbon atoms, m and n together stand for 0 or numbers of 1 to 12 and X stands for halide, alkyl sulfate or alkyl phosphate.

Finally, another group of suitable esterquats are the quaternized ester salts of fatty acids with 1,2-dihydroxypropyl dialkylamines corresponding to formula (III):

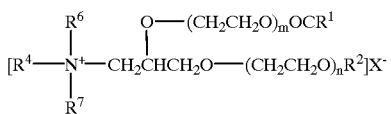

(III)

in which $R^1CO$ is an acyl group containing 6 to 22 carbon atoms, $R^2$ is hydrogen or has the same meaning as $R^1CO$, $R^4$, $R^5$ and $R^7$ independently of one another are alkyl groups containing 1 to 4 carbon atoms, m and n together stand for 0 or numbers of 1 to 12 and X stands for halide, alkyl sulfate or alkyl phosphate.

So far as the choice of the preferred fatty acids and the optimum degree of esterification is concerned, the examples mentioned in regard to (I) also apply to the esterquats of formulae (II) and (III). The esterquats are normally marketed in the form of 50 to 90% by weight alcohol solutions which may readily be diluted with water as required. The esterquats may also be used together with fatty alcohols in the form of flakes, as described for example in German patent DE-C1 4308794 (Henkel).

Chitosans and Chitosan Derivatives

Chitosans (component b) are biopolymers which belong to the group of hydrocolloids. Chemically, they are partly deacetylated chitins differing in their molecular weights which contain the following—idealized—monomer unit:

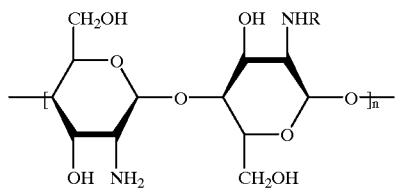

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations (cf. Ullmann's Encyclopedia of Industrial Chemistry, 5th Ed., Vol. A6, Weinheim, Verlag Chemie, 1986, pages 231–332). Overviews of this subject have also been published, for example, by B. Gesslein et al. in HAPPI 27, 57 (1990), O. Skaugrud in Drug Cosm. Ind. 148, 24 (1991) and E. Onsoyen et al. in Seifen-Öle-Fette-Wachse 117, 633 (1991). Chitosans are produced from chitin, preferably from the shell residues of crustaceans which are available in large quantities as inexpensive raw materials. In a process described for the first time by Hackmann et al., the chitin is normally first deproteinized by addition of bases, demineralized by addition of mineral acids and, finally, deacetylated by addition of strong bases, the molecular weights being distributed over a broad spectrum. Corresponding processes are known, for example, from Makromol. Chem. 177, 3589 (1976) or French patent application FR-A 2701266. Preferred types are those which are disclosed in German patent applications DE-A1 4442987 and DE-A1 19537001 (Henkel) and which have an average molecular weight of 800,000 to 1,200,000 dalton, a Brookfield viscosity (1% by weight in glycolic acid) below 5,000 mPas, a degree of deacetylation of 80 to 88% and an ash content of less than 0.3% by weight. Besides the chitosans as typical cationic biopolymers, anionically or nonionically derivatized chitosans such as, for example, the carboxylation, succinylation or alkoxylation products described, for example, in German patent DE-C2 3713099 (L'Oréal) and in German patent application DE-A1 19604180 (Henkel) are also suitable for the purposes of the invention.

Protein Hydrolyzates

Protein hydrolyzates (component c) are degradation products of animal or vegetable proteins, for example collagen, elastin or keratin, preferably almond and potato protein and more particularly wheat, rice and soya protein, which are obtained by acidic, alkaline and/or enzymatic hydrolysis and thereafter have an average molecular weight of 600 to 4,000 and preferably 2000 to 3500. Although protein hydrolyzates are not surfactants in the accepted sense because they lack a hydrophobic residue, they are often used for formulating surface-active compositions by virtue of their dispersing properties. Overviews of the production and use of protein hydrolyzates have been published, for example, by G. Schuster and A. Domsch in Seifen, Öle, Fette, Wachse, 108, 177 (1982) and Cosm. Toil. 99, 63 (1 984), by H. W. Steisslinger in Parf. Kosm. 72, 556 (1991) and by F. Aurich et al. in Tens. Surf. Det. 2, 389 (1992). Vegetable protein hydrolyzates based on wheat gluten or rice protein, of which the production is described in German patents DE-C1 19502167 and DE-C1 19502168 (Henkel), are preferably used.

Alkyl and Alkenyl Oligoalycosides

In one preferred embodiment, the detergent mixtures according to the invention also contain—as component (d)—alkyl and alkenyl oligoglycosides corresponding to formula (IV):

(IV)

in which $R^8$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (IV) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligo-glycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis.

Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12-14}$ cocoalcohol with a DP of 1 to 3 are preferred.

Betaines

In another preferred embodiment, the preparations according to the invention contain surfactants of the betaine type as component (e). Betaines are known surfactants which are mainly obtained by carboxyalkylation, preferably carboxymethylation, of aminic compounds. The starting materials are preferably condensed with halocarboxylic acids or salts thereof, especially sodium chloroacetate, 1 mole of salt being formed per mole of betaine. Another suitable method is the addition of unsaturated carboxylic acids, for example acrylic acid. Information on the nomenclature and above all on the difference between betaines and "true" amphoteric surfactants can be found in the article by U. Ploog in Seifen-Öle-Fette-Wachse, 198. 373 (1982). Other overviews on this subject have been published, for example, by A. O'Lennick et al. in HAPPI, Nov. 70 (1986), by S. Holzman et al. in Tens. Det. 23, 309 (1986), by R. Bibo et al. in Soap Cosm. Chem. Spec. Apr. 46 (1990) and by P. Ellis et al. in Euro Cosm. 1, 14 (1994). Examples of suitable betaines are the carboxy-alkylation products of secondary and, more particularly, tertiary amines corresponding to formula (V):

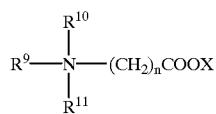

(V)

in which $R^9$ represents alkyl and/or alkenyl groups containing 6 to 22 carbon atoms, $R^{10}$ represents hydrogen or alkyl groups containing 1 to 4 carbon atoms, $R^{11}$ represents alkyl groups containing 1 to 4 carbon atoms, n is a number of 1 to 6 and X is an alkali metal and/or alkaline earth metal or ammonium. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof.

Also suitable are carboxyalkylation products of amidoamines which correspond to formula (VI):

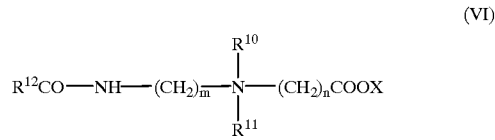

where $R^{12}CO$ is an aliphatic acyl group containing 6 to 22 carbon atoms and 0 or 1 to 3 double bonds, m is a number of 1 to 3 and $R^{10}$, $R^{11}$, n and X are as defined above. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethylamino-ethyl amine, N,N-dimethylaminopropyl amine, N,N-diethylaminoethyl amine and N,N-diethylaminopropyl amine which are condensed with sodium chloroacetate. A condensation product of $C_{8/18}$ coco-fatty acid-N,N-dimethylaminopropyl amide with sodium chloroacetate is preferably used.

Detergent Mixtures

In one preferred embodiment of the invention, the detergent mixtures are used in the form of aqueous preparations with a solids content of 15 to 70, preferably 25 to 50 and more preferably 35 to 45% by weight. Based on the solids content, the mixtures may contain components (a) to (e) in the following quantities:

(a) 10 to 60, preferably 20 to 40% by weight esterquats,
(b) 1 to 10, preferably 2 to 5% by weight chitosan and/or chitosan derivatives,
(c) 10 to 30, preferably 5 to 20% by weight protein hydrolyzates,
(d) 0 to 25, preferably 5 to 20% by weight alkyl and/or alkenyl oligoglycosides and
(e) 0 to 25, preferably 5 to 20% by weight betaines, with the proviso that the quantities by weight shown add up to 100% by weight.

Commercial Applications

The detergent mixtures according to the invention have excellent cleaning performance and provide synthetic and natural fibers with a pleasant soft feel. They also reduce the electrostatic charging between the fibers and improve their rewettability. Accordingly, the present invention also relates to the use of the mixtures for the production of surface-active compositions such as, for example, laundry detergents, dishwashing detergents, cleaners and conditioners and cosmetic preparations such as, in particular, hair-care and body-care products.

Laundry Detergents Dishwashing Detergents and Cleaners

Typical examples of laundry detergents, dishwashing detergents and cleaners which may contain the detergent mixtures according to the invention are liquid to paste-form fabric softeners, manual dishwashing detergents, machine dishwashing detergents, rinse aids and multipurpose, household and sanitary cleaners, powder-form and granular heavy-duty detergents and, in particular, conditioners. The preparations may contain other typical ingredients such as, for example, detergent surfactants, builders, enzymes, enzyme stabilizers, bleaching agents, optical brighteners, thickeners, soil repellents, foam inhibitors, solubilizers, inorganic salts and dyes and perfumes.

Typical detergent surfactants are alkyl benzenesulfonates, alkyl sulfates, sulfofatty acids, sulfofatty acid methylesters and the like. Suitable builders are zeolites, layered silicates, phosphates and ethylenediamine tetraacetic acid, nitrilotri-acefic acid, citric acid and inorganic phosphonic acids.

Among the compounds serving as peroxy bleaching agents, sodium perborate tetrahydrate and sodium perborate monohydrate are particularly important. Other bleaching agents are, for example, peroxycarbonate, citrate perhydrates and $H_2O_2$-yielding peracidic salts of per acids, such as perbenzoates, peroxyphthalates or diperoxydodecane diacid. They are normally used in quantities of 8 to 25% by weight. It is preferred to use sodium perborate monohydrate in quantities of 10 to 20% by weight and more particularly 10 to 15% by weight. By virtue of its ability to bind free water with formation of the tetrahydrate, it contributes towards increasing the stability of the composition.

Suitable thickeners are, for example, hydrogenated castor oil, salts of long-chain fatty acids, which are preferably used in quantities of 0 to 5% by weight and more particularly in quantities of 0.5 to 2% by weight, for example sodium, potassium, aluminium, magnesium and titanium stearates or the sodium and/or potassium salts of behenic acid, and other polymeric compounds. Preferred other polymeric compounds are polyvinyl pyrrolidone, urethanes and the salts of polymeric polycarboxylates, for example homopolymeric or copplymeric polyacrylates, polymethacrylates and, more particularly, copolymers of acrylic acid with maleic acid, preferably those of 50 to 10% of maleic acid. The relative molecular weight of the homopolymers is generally between 1,000 and 100,000 and that of the copolymers between 2,000 and 200,00 and preferably between 50,000 and 120,000, based on the free acid. Other suitable thickeners are in particular water-soluble polyacrylates which are crosslinked, for example, with about 1% of a polyallylether of sucrose and which have a relative molecular weight above 1,000,000. Examples of such products are the polymers obtainable under the names of Carbopol® 940 and Carbopol® 941. The crosslinked polyacrylates are preferably used in quantities of not more than 1% by weight and more preferably in quantities of 0.2 to 0.7% by weight.

Suitable enzymes are enzymes from the class of proteases, lipases, amylases, cellulases and mixtures thereof. Enzymes obtained from bacterial strains or fungi, such as Bacillus subtilis, Bacillus licheniformis and Streptomyces griseus are particularly suitable. Proteases of the subtilisin type are preferably used, proteases obtained from Bacillus lentus being particularly preferred. They may make up from about 0.2 to 2% by weight of the mixture. The enzymes may be adsorbed to supports and/or encapsulated in shell-forming substances to protect them against premature decomposition.

In addition to mono- and polyhydric alcohols and phosphonates, the detergents may contain other enzyme stabilizers. For example, 0.5 to 1% by weight of sodium formate may be used. Proteases stabilized with soluble calcium salts and having a calcium content of preferably about 1.2% by weight, based on the enzyme, may also be used. However, it is of particular advantage to use boron compounds, for example boric acid, boron oxide, borax and other alkali metal borates, such as the salts of orthoboric acid ($H_3BO_3$), metaboric acid ($HBO_2$) and pyroboric acid (tetraboric acid $H_2B_4O_7$).

Where the compositions are used in washing machines, it can be of advantage to add typical foam inhibitors to them. Suitable foam inhibitors contain, for example, known organopolysiloxanes, paraffins or waxes.

Cosmetic Preparations

If the detergent mixtures according to the invention are used for the production of cosmetic preparations, such as for example hair shampoos, hair lotions, foam baths, cremes or lotions, these preparations may also contain other mild surfactants, oil components, emulsifiers, superfatting agents, pearlizing waxes, stabilizers, consistency factors, thickeners, cationic polymers, silicone compounds, biogenic agents, anti-dandruff agents, film formers, preservatives, hydrotropes, solubilizers, UV filters, insect repellents, self-tanning agents, perfume oils, dyes and the like as further auxiliaries and additives.

Typical examples of suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, fatty acid glucamides and/or protein fatty acid condensates (preferably based on wheat proteins).

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono/di-/triglyceride mixtures based on $C_{6-18}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, Guerbet carbonates, esters of benzoic acid with linear and/or branched $C_{6-22}$ alcohols (for example Finsolv®TN), dialkyl ethers, ring opening products of epoxidized fatty acid esters with polyols, silicone oils and/or aliphatic or naphthenic hydrocarbons.

Suitable emulsifiers are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of products of the addition of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) adducts of 15 to 60 moles of ethylene oxide with castor oil and/or hydrogenated castor oil;

(5) polyol esters and, in particular, polyglycerol esters such as, for example, polyglycerol polyricinoleate or polyglycerol poly-12-hydroxystearate. Mixtures of compounds from several of these classes are also suitable;

(6) products of the addition of 2 to 15 moles of ethylene oxide with castor oil and/or hydrogenated castor oil;

(7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(8) trialkyl phosphates and mono-, di- and/or tri-PEG-alkyl phosphates;

(9) wool wax alcohols;

(10) polysiloxane/polyalkyl polyether copolymers and corresponding derivatives;

(11) mixed esters of pentaerythritol, fatty acids, citric acid and fatty alcohol according to DE-PS 1165574 and/or mixed esters of fatty acids containing 6 to 22 carbon atoms, methyl glucose and polyols, preferably glycerol, and

(12) polyalkylene glycols.

The addition products of ethylene oxide and/or propylene oxide with fatty alcohols, fatty acids, alkylphenbls, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols containing 12 to 22 and preferably 16 to 18 carbon atoms and also partial glycerides. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol mono-esters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethox-ylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryidimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylamino-hydroxypropyl diethylenetriamine (Cartaretine®), Sandoz), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable silicone compounds are, for example, dimethyl polysiloxanes, methylphenyl polysiloxanes, cyclic silicones and amino-, fatty acid-, alcohol-, polyether-, epoxy-, fluorine-, and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate may be used as stabilizers. In the context of the invention, blogenic agents are, for example, tocopherol, tocopherol acetate, tocopherol palmitate, ascorbic acid, retinol, bisabolol, allantoin, phytantriol, panthenol, AHA acids, amino acids, ceramides, pseudoceramides, essential oils, plant extracts, proteolytic enzymes and vitamin complexes. Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidonelvinyl acetate copolymers, polymers of the acrylic acid series, quaternary cellulose derivatives, collagen, hyaluronic acid and salts thereof and similar compounds. Suitable swelling agents for aqueous phases are montmorillonites, clay minerals, Pemulen and alkyl-modified Carbopol types (Goodrich).

In the context of the invention, UV filters are organic compounds which are capable of absorbing ultraviolet rays and of releasing the energy absorbed in the form of longer wave radiation, for example heat. Typical examples are 4-aminobenzoic acid and esters and derivatives thereof (for example 2-ethylhexyl-p-dimethylaminobenzoate or p-dimethylaminobenzoic acid octyl ester), methoxycinnamic acid and derivatives thereof (for example 4-methoxycinnamic acid-2-ethylhexyl ester), benzophenones (for example oxybenzone, 2-hydroxy-4- methoxybenzophenone), dibenzoyl methanes, salicylate esters, 2-phenylbenzimidazole-5-sulfonic acid, 1-(4-tert.butylphenyl)-3-(4'-methoxyphenyl)-propane-1,3-dione, 3-(4'-methyl)-benzylidenebornan-2-one, methylbenzylidene camphor and the like. Other suitable UV filters are finely disperse metal oxides and salts, for example-titanium dioxide, zinc oxide, iron oxide, aluminium oxide, cerium oxide, zirconium oxide, silicates (talcum) and barium sulfate. The particles should have an average diameter of less than 100 nm, preferably from 5 to 50 nm and more preferably from 15 to 30 nm. They may be spherical in shape although ellipsoidal particles or other non-spherical particles may also be used. Besides the two above-mentioned groups of primary light filters, secondary light filters of the antioxidant type, which interrupt the photochemical reaction chain initiated when UV radiation penetrates into the skin, may also be used. Typical examples of these secondary light filters are Superoxid-Dismutase, tocopherols (vitamin E) and ascorbic acid (vitamin C).

In addition, hydrotropes, such as, for example, ethanol, isopropyl alcohol or polyols may be used to improve flow behavior., Suitable polyols preferably contain 2 to 15 carbon atoms and at least two hydroxyl groups.

Typical Examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formaldehyde solution, parabens, pentanediol or sorbic acid. Suitable Insect repellents are N,N-diethyl-m-toluamide, pentane-1,2-diol or Insect Repellent 3535. A suitable self-tanning agent is dihydroxyacetone.

Suitable perfume oils include the extracts of blossoms (lavender, rose, jasmine, neroli), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Suitable synthetic or semisynthetic perfume oils are Ambroxan, eugenol, isoeugenol, citronellal, hydroxy-citronellal, geraniol, citronellol, geranyl acetate, citral, ionone and methyl ionone.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemle, Weinheim, 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be prepared by standard cold or hot processes and are preferably produced by the phase inversion temperature method.

EXAMPLES

The dermatological compatibility of the detergent mixtures was determined by OECD Method No. 404 and EEC Directive 94/449 EEC, Pt.B.4. The total irritation scores shown were derived from the irritation scores obtained after 24, 48 and 72 h. The total irritation score determined in Comparison Example 1 was put at 100% and the scores obtained in the other Examples were related to that total.

To determine cleaning performance, soiled cotton fabric (soil: dust/sebum) -was washed in a Launder-o-meter at 60° C. with 1 g of the preparations and 1 g of zeolite and whiteness (% reflectance) was photometrically determined against barium sulfate as standard.

Softness was evaluated by a panel of 6 trained people who evaluated the washed cotton fabric on a scale of (1)=very soft to (4)=hard.

The hydrophilia, i.e. the rewettability of the fabric, was determined by the known height-of-rise test according to DIN 53924 in which 1 cm wide strips of the cotton fabric were placed in water and the height to which the water rises in the fabric in 1 minute under the effect of the capillary forces is measured: the greater the height to which the water rises, the greater the hydrophilia of the fabric.

Wet combability was tested on brown hair (Alkinco #6634, tress length 12 cm, tress weight 1 g). After the zero measurement, the tresses were soaked with 1000 ml of the formulations. After a contact time of 5 minutes, the tresses were rinsed out in running water (1 l/min. 38° C.). The tresses were remeasured and compared with the zero measurement. The average error in the measurements was 2%, the statistical certainty was 99%.

The results are set out in Table 1. Examples 1 to 8 correspond to the invention, Examples C1 and C2 are intended for comparison.

TABLE I

| | Composition and performance of detergent mixtures | | | | | | | | | | |
|---|---|---|---|---|---|---|---|---|---|---|---|
| Composition/Performance | 1 | 2 | 3 | 4 | 5 | 6 | 7 | 8 | C1 | C2 | C3 |
| Esterquat* | 35 | 35 | 20 | 20 | 20 | 20 | 20 | 20 | — | — | 35 |
| Distearyldimethyl ammonium chloride (QUAT) | — | — | — | — | — | — | — | — | 35 | 20 | — |
| Chitosan | 1 | — | 1 | 1 | 1 | — | — | — | 1 | 1 | — |
| Succinylated chitosan | — | 1 | — | — | — | 1 | 1 | 1 | — | — | — |
| Wheat Protein Hydrolyzate | 14 | 14 | 9 | 9 | 9 | 9 | 9 | 9 | 14 | 9 | 14 |

TABLE I-continued

Composition and performance of detergent mixtures

| Composition/Performance | 1 | 2 | 3 | 4 | 5 | 6 | 7 | 8 | C1 | C2 | C3 |
|---|---|---|---|---|---|---|---|---|---|---|---|
| Coco Glucosides | — | — | 20 | — | 10 | 20 | — | 10 | — | 20 | — |
| Cocamidopropyl Betaine | — | — | — | 20 | 10 | — | 20 | 10 | — | — | — |
| Water | | | | | | to 100 | | | | | |
| Total irritation score [%-rel] | 85 | 88 | 76 | 78 | 68 | 77 | 79 | 69 | 100 | 90 | 95 |
| Whiteness [%-refl.] | 59.7 | 60.1 | 75.8 | 76.5 | 78.2 | 74.4 | 75.0 | 73.9 | 52.5 | 66.8 | 60.3 |
| Softness | 1.5 | 1.5 | 1.0 | 1.0 | 1.0 | 1.0 | 1.0 | 1.0 | 2.5 | 2.5 | 2.0 |
| Hydrophilia [mm] | 11 | 12 | 11 | 13 | 12 | 11 | 11 | 11 | 8 | 9 | 10 |
| Wet combability [mV] | 44.3 | 45.7 | 50.1 | 51.0 | 49.8 | 49.7 | 49.5 | 50.0 | 36.1 | 37.0 | 40.0 37.0 |

*Methyl-quaternized dipalm oil fatty acid triethanolamine ester, methyl sulfate salt

What is claimed is:

1. A surface-active composition comprising:
   (a) an esterquat;
   (b) a chitosan and/or chitosan derivative; and
   (c) a protein hydrolyzate.

2. The composition of claim 1 wherein the chitosan and/or chitosan derivative has an average molecular weight of from 800,000 to 1,200,000 dalton, a Brookfield viscosity below 5000 mPas, a degree of deacetylation of from 80 to 88% and an ash content of less than 0.3% by weight.

3. The composition of claim 1 wherein the protein hydrolyzate is derived from a vegetable.

4. The composition of claim 1 wherein the esterquat is present in the composition in an amount of from 10 to 60% by weight, based on the weight of the composition.

5. The composition of claim 1 wherein the chitosan and/or chitosan derivative is present in the composition in an amount of from 1 to 10% by weight, based on the weight of the composition.

6. The composition of claim 1 wherein the protein hydrolyzate is present in the composition in an amount of from 10 to 30% by weight, based on the weight of the composition.

7. The composition of claim 1 further comprising an alkyl and/or alkenyl oligoglycoside.

8. The composition of claim 7 wherein the alkyl and/or alkenyl oligoglycoside is present in the composition in an amount of up to 25% by weight, based on the weight of the composition.

9. The composition of claim 1 further comprising a betaine present in an amount of up to 25% by weight, based on the weight of the composition.

10. A surface-active composition comprising:
    (a) from 20 to 40% by weight of an esterquat;
    (b) from 2 to 5% by weight of a chitosan and/or chitosan derivative; and
    (c) from 5 to 20% by weight of a protein hydrolyzate, all weights being based on the total weight of the composition.

11. A process for cleaning a substrate comprising contacting the substrate with a surface-active composition containing:
    (a) an esterquat;
    (b) a chitosan and/or chitosan derivative; and
    (c) a protein hydrolyzate.

12. The process of claim 11 wherein the chitosan and/or chitosan derivative has an average molecular weight of from 800,000 to 1,200,000 dalton, a Brookfield viscosity below 5000 mPas, a degree of deacetylation of from 80 to 88% and an ash content of less than 0.3% by weight.

13. A The process of claim 11 wherein the protein hydrolyzate is derived from a vegetable.

14. The process of claim 11 wherein the esterquat is present in the composition in an amount of from 10 to 60% by weight, based on the weight of the composition.

15. The process of claim 11 wherein the chitosan and/or chitosan derivative is present in the composition in an amount of from 1 to 10% by weight, based on the weight of the composition.

16. The process of claim 11 wherein the protein hydrolyzate is present in the composition in an amount of from 10 to 30% by weight, based on the weight of the composition.

17. The process of claim 11 wherein the composition further comprises an alkyl and/or alkenyl oligoglycoside.

18. The process of claim 17 wherein the alkyl and/or alkenyl oligoglycoside is present in the composition in an amount of up to 25% by weight, based on the weight of the composition.

19. The process of claim 11 wherein the composition further comprises a betaine present in an amount of up to 25% by weight, based on the weight of the composition.

* * * * *